United States Patent
Ohishi et al.

(10) Patent No.: US 7,412,023 B2
(45) Date of Patent: Aug. 12, 2008

(54) X-RAY DIAGNOSTIC APPARATUS

(75) Inventors: Satoru Ohishi, Otawara (JP); Kenneth Richard Hoffmann, Williamsville, NY (US)

(73) Assignees: Toshiba Medical Systems Corporation, Otawara-shi (JP); The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/362,738

(22) Filed: Feb. 28, 2006

(65) Prior Publication Data

US 2007/0201609 A1 Aug. 30, 2007

(51) Int. Cl.
*A61B 6/00* (2006.01)

(52) U.S. Cl. ............... 378/4; 378/98.11; 378/98.12

(58) Field of Classification Search ............ 378/4–20, 378/98.11, 98.12, 210, 901; 382/131, 132
See application file for complete search history.

(56) References Cited

U.S. PATENT DOCUMENTS

| | | | | |
|---|---|---|---|---|
| 4,029,963 A * | 6/1977 | Alvarez et al. | ............. | 378/5 |
| 5,048,103 A * | 9/1991 | Leclerc et al. | ............. | 382/294 |
| 5,802,133 A * | 9/1998 | Kawai et al. | ............. | 378/4 |
| 5,839,440 A * | 11/1998 | Liou et al. | ............. | 600/431 |
| 6,188,744 B1 * | 2/2001 | Shinohara et al. | ............. | 378/8 |
| 6,195,450 B1 * | 2/2001 | Qian et al. | ............. | 382/130 |
| 6,196,715 B1 * | 3/2001 | Nambu et al. | ............. | 378/197 |
| 6,614,874 B2 * | 9/2003 | Avinash | ............. | 378/62 |
| 6,661,873 B2 * | 12/2003 | Jabri et al. | ............. | 378/98.11 |
| 6,714,629 B2 * | 3/2004 | Vilsmeier | ............. | 378/165 |
| 2003/0016850 A1 * | 1/2003 | Kaufman et al. | ............. | 382/128 |
| 2003/0031299 A1 * | 2/2003 | Ohishi | ............. | 378/162 |
| 2003/0215055 A1 * | 11/2003 | Ozawa et al. | ............. | 378/62 |
| 2005/0129299 A1 * | 6/2005 | Kreang-Arekul et al. | ............. | 382/132 |
| 2006/0210019 A1 * | 9/2006 | Rasche et al. | ............. | 378/62 |

* cited by examiner

*Primary Examiner*—Courtney Thomas
*Assistant Examiner*—Alexander H Taningco
(74) *Attorney, Agent, or Firm*—Oblon, Spivak, McClelland, Maier & Neustadt, P.C.

(57) ABSTRACT

A X-ray diagnostic apparatus includes an X-ray imaging unit including an X-ray tube and an X-ray detecting unit to generate an X-ray image, an image generating unit generating a 3D non-blood vessel image and a 3D blood vessel image from an original 3D image generated by the X-ray diagnostic apparatus or an X-ray CT apparatus, a projection image generating unit generating a non-blood vessel projection image from the 3D non-blood vessel image and generating a blood vessel projection image from the 3D blood vessel image, a positional shift identifying unit identifying a positional shift between the X-ray image and the non-blood vessel projection image, a correcting unit correcting a positional shift of the blood vessel projection image on the basis of the positional shift, and a display unit which displays the X-ray image and the corrected blood vessel projection image.

27 Claims, 4 Drawing Sheets

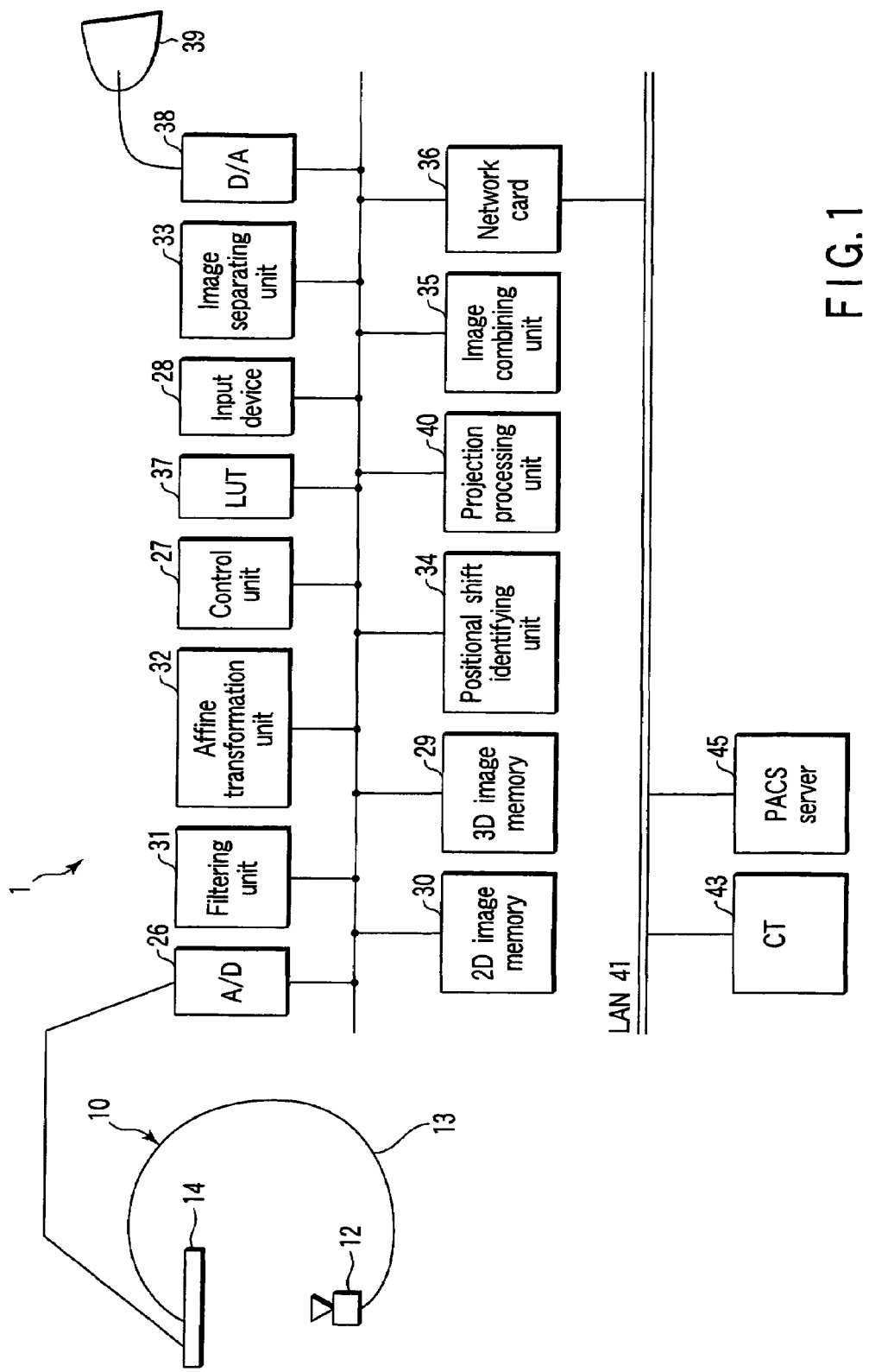
F I G. 1

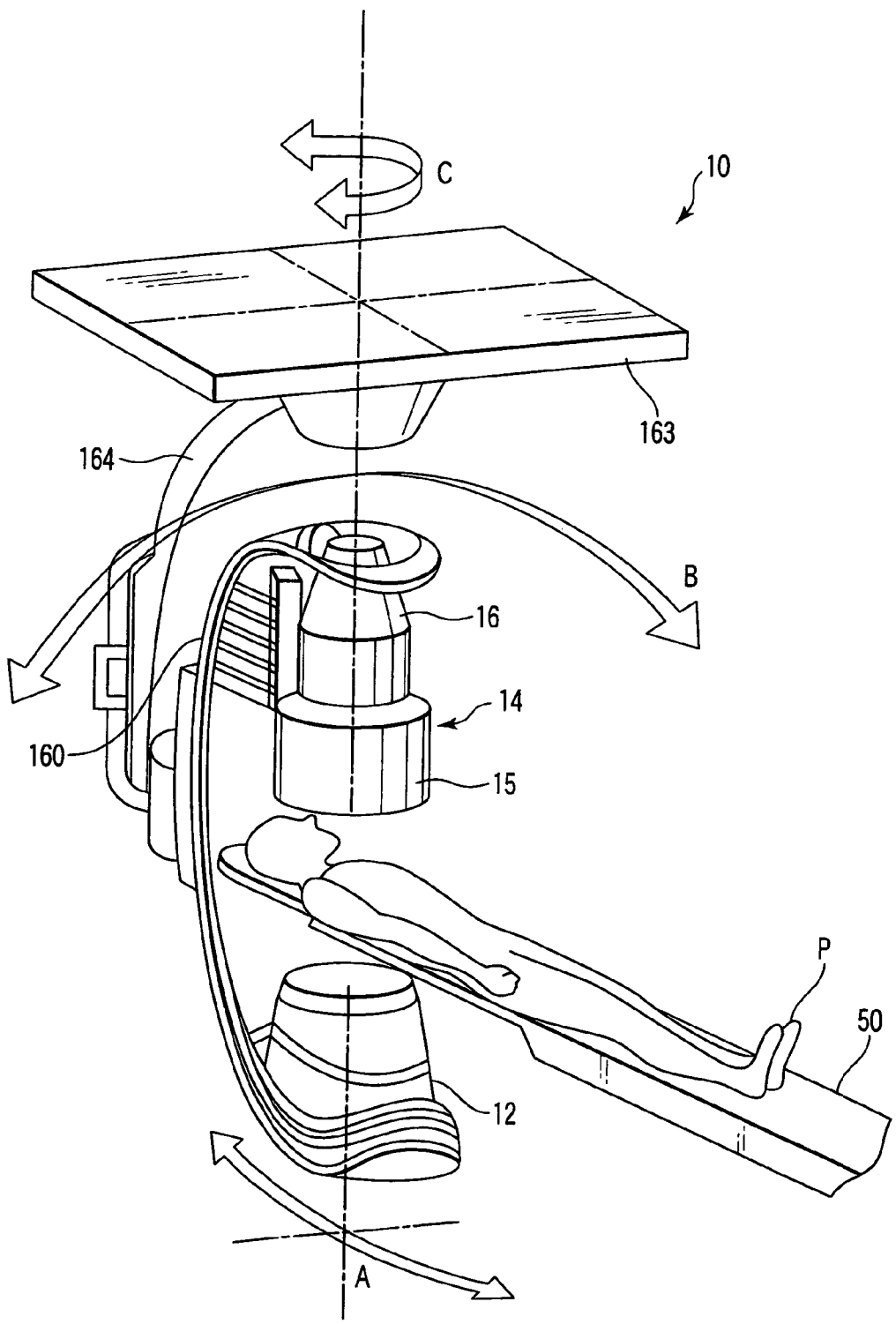
F I G. 2

X-RAY DIAGNOSTIC APPARATUS

BACKGROUND OF THE INVENTION

1. Field of the Invention

The present invention relates to an X-ray diagnostic apparatus generating a road map for a blood vessel structure.

2. Description of the Related Art

In intervention or angiographic examination, a catheter is inserted into a blood vessel from, for example, the joint of a leg and is guided to a target region through the blood vessel. This catheter or a guide wire inserted in the catheter is pushed forward to a target position under X-ray fluoroscopic observation. However, the blood vessel cannot be seen in an X-ray image unless enhanced by a contrast medium. Keeping injecting the contrast medium to visualize the blood vessel may result in renal failure. For this reason, a road map function is provided, which displays an image sensed after a contrast medium is injected once and an X-ray fluoroscopic image upon superimposing them. This function allows the operator to discriminate the position of a blood vessel to a certain extent without injecting any contrast medium, and hence is often used especially when a blood vessel structure is complicated and it is difficult to push a catheter or a guide wire into the blood vessel. According to this road map function, however, the occurrence of movement of the bed, rotation of the arm to change the observation direction, slight movement (stirring) of the patient, or the like makes it necessary to re-generate a road map image. Frequently re-generating a road map image leads to increases in examination time and the amount of contrast medium used.

In order to solve such problems, a 3D road map in which a road map image generated by using a 3D image and a fluoroscopic image are superimposed on each other is expected to be effective in reducing the amount of contrast medium used and shortening the examination time.

In order to mechanically superimpose a 3D image and an X-ray image, a method of generating a positional shift table may be used. However, since no specific limitation is imposed on angles to be used for medical treatment, a large amount of calibration data is required. This method cannot follow up the movement of a patient during medical treatment.

In academic conferences and the like, there has been proposed a method of performing calibration by extracting a catheter from a fluoroscopic image assuming that the catheter travels through a blood vessel. In a region with a complicated blood vessel structure, however, there is a risk of misinterpreting the correspondence between blood vessels. In addition, the shape of a blood vessel may be changed by the catheter. Furthermore, if a patient moves, it is very difficult to make correction by using the above method.

BRIEF SUMMARY OF THE INVENTION

It is an object of the present invention to cope with the movement of a patient while eliminating the necessity to generate a positional shift table by positioning a non-blood vessel image and an X-ray image without mechanically superimposing them. It is another object of the present invention to show the positional shift between a 3D image and a fluoroscopic image to an operator by displaying a fluoroscopic image and a non-blood vessel image upon superimposing them after positioning.

According to a first aspect of the present invention, there is provided an X-ray diagnostic apparatus comprising an X-ray imaging unit which has an X-ray tube and an X-ray detecting unit to generate an X-ray image, an image generating unit which generates a 3D non-blood vessel image and a 3D blood vessel image from an original 3D image generated by the X-ray diagnostic apparatus or an X-ray CT apparatus, a projection image generating unit which generates a non-blood vessel projection image from the 3D non-blood vessel image and generates a blood vessel projection image from the 3D blood vessel image, a positional shift identifying unit which identifies a positional shift between the X-ray image and the non-blood vessel projection image, a correcting unit which corrects a positional shift of the blood vessel projection image on the basis of the positional shift, and a display unit which displays the X-ray image and the corrected blood vessel projection image.

According to a second aspect of the present invention, there is provided an X-ray diagnostic apparatus comprising an X-ray imaging unit which has an X-ray tube and an X-ray detecting unit to generate an X-ray image, an image generating unit which generates a 3D non-blood vessel image and a 3D blood vessel image from an original 3D image generated by the X-ray diagnostic apparatus or an X-ray CT apparatus, a projection image generating unit which generates a non-blood vessel projection image from the 3D non-blood vessel image and generates a blood vessel projection image from the 3D blood vessel image, a positional shift identifying unit which identifies a positional shift between the X-ray image and the non-blood vessel projection image, a correcting unit which corrects a positional shift of the blood vessel projection image on the basis of the positional shift, and a combining unit which combines the X-ray image and the corrected blood vessel projection image.

According to a third aspect of the present invention, there is provided an X-ray diagnostic apparatus comprising an X-ray imaging unit which has an X-ray tube and an X-ray detecting unit to generate an X-ray image, an image generating unit which generates a 3D non-blood vessel image and a 3D blood vessel image from an original 3D image generated by the X-ray diagnostic apparatus or an X-ray CT apparatus, a projection image generating unit which generates a non-blood vessel projection image from the 3D non-blood vessel image and generates a blood vessel projection image from the 3D blood vessel image, a positional shift identifying unit which identifies a positional shift between the X-ray image and the non-blood vessel projection image, and a combining unit which combines the X-ray image and the corrected blood vessel projection image on the basis of the positional shift.

According to a fourth aspect of the present invention, there is provided an image processing apparatus comprising a storage unit which stores an X-ray image, 3D non-blood vessel image, and 3D blood vessel image associated with the same subject, a projection image generating unit which generates a non-blood vessel projection image from the 3D non-blood vessel image and generates a blood vessel projection image from the 3D blood vessel image, a positional shift identifying unit which identifies a positional shift between the X-ray image and the non-blood vessel projection image, and a combining unit which combines the X-ray image and the corrected blood vessel projection image on the basis of the positional shift.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing the arrangement of an X-ray diagnostic apparatus according to an embodiment of the present invention;

FIG. 2 is a perspective view of an X-ray imaging mechanism in FIG. 1;

DETAILED DESCRIPTION OF THE INVENTION

Figure 3:
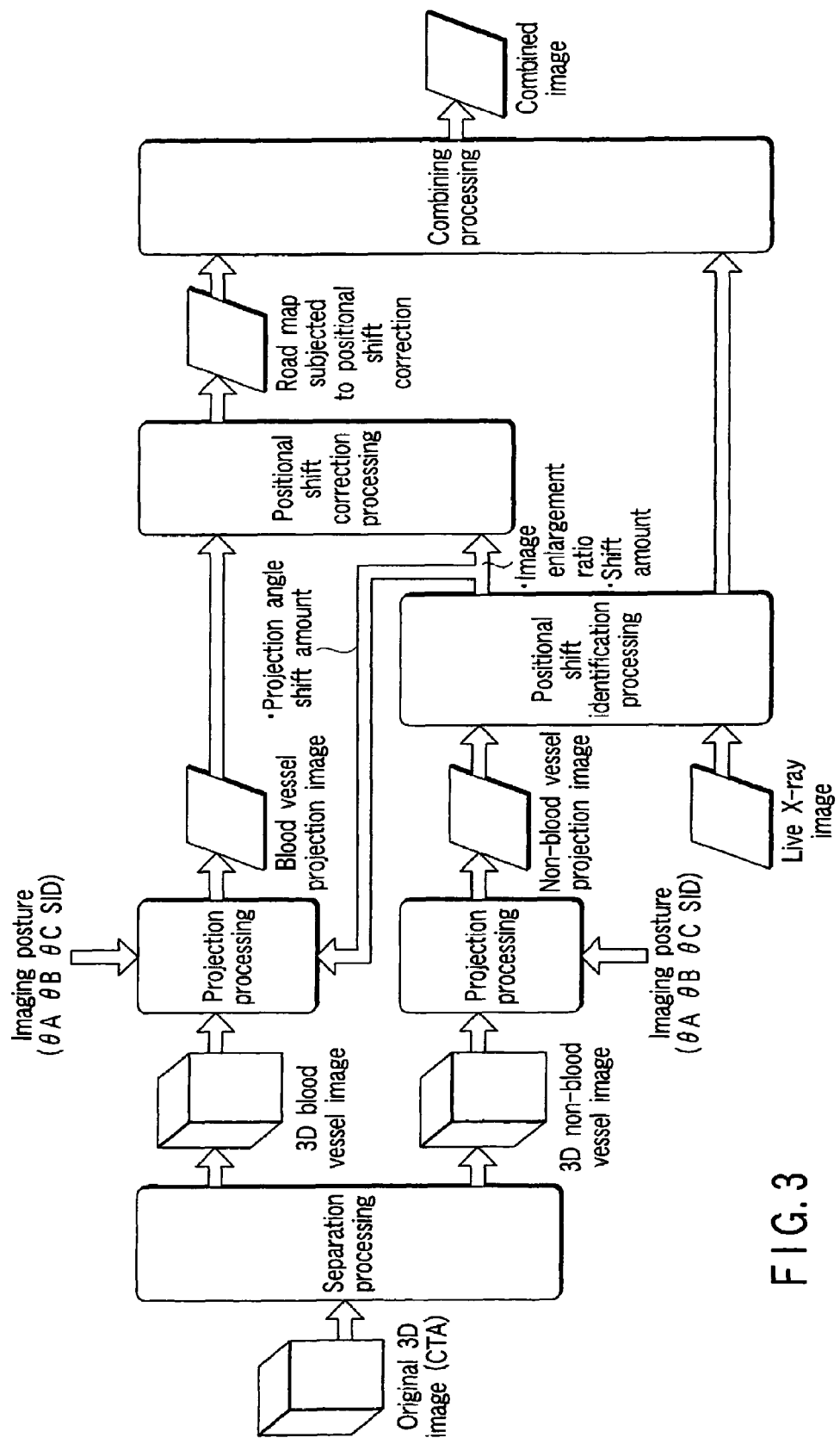
FIG. 3 is a view showing a processing sequence in this embodiment.

As shown in FIG. 1, an X-ray diagnostic apparatus includes an X-ray imaging mechanism 10 and an image processing apparatus 1. As shown in FIG. 2, the X-ray imaging mechanism 10 includes an X-ray tube 12 and an X-ray detector 14. The X-ray detector 14 comprises an image intensifier 15 and a TV camera 16. Note that the X-ray detector 14 may comprise a flat panel detector (FPD) having semiconductor detection elements arranged in the form of a matrix instead of the combination of the image intensifier 15 and the TV camera 16. The X-ray tube 12 is mounted on a C-arm 160, together with the X-ray detector 14. A subject P on a top 50 of the bed is placed between the X-ray tube 12 and the X-ray detector 14. The C-arm 160 is supported on an arcuated column 164 suspended from a ceiling base 163. The C-arm 160 is rotatable in orthogonal axes A, B, and C.

The image processing apparatus 1 is connected to the X-ray detector 14 through an analog/digital converter (A/D) 26. In addition to the analog/digital converter (A/D) 26, the image processing apparatus 1 comprises a control unit 27, input device 28, 2D image memory 30, 3D image memory 29, filtering unit 31, affine transformation unit 32, image separating unit 33, positional shift identifying unit 34, image combining unit 35, network card 36, lookup table (LUT) 37, digital/analog converter (D/A) 38, display 39, and projection processing unit 40. The input device 28 has a road map switch for inputting a user instruction to combine a road map of blood vessels with the current X-ray image (final X-ray image).

The 3D image memory 29 stores 3D image data associated with a target region of a subject which is input from an external X-ray computerized tomographic apparatus 43 or a PACS server 45 through a local area network (LAN) and the network card 36. 3D image data is typically 3D image data of a subject injected with a contrast medium which is generated by the X-ray computerized tomographic apparatus 43 with a blood vessel being enhanced, i.e., so-called 3D CTA (CT Angiography) image data. The 3D image memory 29 stores 3D non-blood vessel image data and 3D blood vessel image data separated from 3D CTA image data by the image separating unit 33. 3D blood vessel image data has an enhanced blood vessel region which can be extracted by threshold processing. 3D non-blood vessel data has a region associated with a bone and soft tissue, other than a blood vessel region, which is obtained by subtracting 3D blood vessel image data from the 3D CTA image data.

The 2D image memory 30 stores 2D X-ray image data generated by the X-ray imaging mechanism 10, 2D X-ray image data subjected to filtering such as high-frequency enhancement by the filtering unit 31, 2D X-ray image data subjected to affine transformation such as image enlargement/movement by the affine transformation unit 32, blood vessel projection image data generated from 3D blood vessel image data by projection processing by the projection processing unit 40, and non-blood vessel projection image data generated from non-blood vessel projection image data by projection processing by the projection processing unit 40.

The positional shift identifying unit 34 calculates the anatomical positional shift of a non-blood vessel projection image (to be referred to as a positional shift identification image as needed hereinafter) generated by projection processing by the projection processing unit 40, in accordance with the imaging posture of the X-ray imaging mechanism 10 at the time when the road map switch is pressed, with respect to 2D X-ray image (to be referred to as a final X-ray image hereinafter) generated by the X-ray imaging mechanism 10 at the time when the road map switch is pressed. Note that an imaging posture is determined by the angles ($\theta A$, $\theta B$, and $\theta C$) of the C-arm 160 with respect to arrows A, B, and C and the SID (the distance between the X-ray tube 12 and the isocenter). In addition, a positional shift amount is defined as the degree of anatomical spatial error of a subject on a positional shift identification image with respect to a final X-ray image. More specifically, a positional shift amount is defined as the difference in image enlargement ratio between a final X-ray image and a positional shift identification image, the spatial displacement amount (to be referred to as a shift amount) of a non-blood vessel image of a subject on a positional shift identification image with respect to a final X-ray image, or the shift amount (angular difference) of the projection angle of a positional shift identification image with respect to the imaging angle of a final X-ray image.

The projection processing unit 40 generates a blood vessel projection image (to be referred to as a road map) from 3D blood vessel image data by projection processing in accordance with the projection angle determined by an imaging posture and the shift amount of a calculated projection angle. The affine transformation unit 32 performs enlargement processing for this blood vessel projection image to attain matching of an enlargement ratio and shifts the image (positional shift correction processing) in accordance with a shift amount to attain spatial matching. The image combining unit 35 combines a road map having undergone positional shift correction with a final X-ray image. In the lookup table 37, a specific color is assigned to the road map portion of this combined image. The display 39 displays the combined image.

FIG. 3 shows the flow of processing in this embodiment. Intervention or medical treatment is started upon inputting of examination information such as a patient name, specific patient number (patient ID), examination program, and examination date. 3D CTA data concerning the same region of the corresponding subject (patient) is loaded from the CT apparatus 43, the PACS server 45 which manages CT data, or the like into the 3D image memory 29 through a network 41 such as a LAN. Note that 3D CTA data contains an image of a non-blood vessel region other than a blood vessel and an image of a blood vessel region enhanced with a contrast medium. For the sake of descriptive convenience, 3D CTA data will be referred to as an original 3D image.

An original 3D image is automatically separated into a 3D non-blood vessel image and a 3D blood vessel image by the image separating unit 33 on the basis of CT values. Typically, a 3D blood vessel image is extracted from an original 3D image by threshold processing, and a 3D non-blood vessel image is extracted by subtracting the 3D blood vessel image from the original 3D image. The 3D blood vessel image data and the 3D non-blood vessel image data are stored in the 3D image memory 29. For example, data corresponding to the interval between a CT value of 120 and a CT value of 300 is separated as a 3D blood vessel image from CTA data, and the remaining data is separated as a 3D non-blood vessel image. At this time, of the 3D non-blood vessel image, a region recognized as a blood vessel portion (a region corresponding to the interval between a CT value of 120 and a CT value of 300) is set to, for example, 0 as the standard CT value of soft tissue. Note that this CT value changes depending on the concentration and type of contrast medium to be used, contrast conditions, and the like. It is therefore preferable to set a CT value for each site.

When intervention or medical treatment is started, the catheter is inserted into the blood vessel and guided to a target position, e.g., a blood vessel in the head. In this process, it may be difficult to insert the catheter into a target branch portion. In such a case, a 3D road map is used so that the operator can comprehend the shape of the branch portion and easily insert the catheter into it.

When the operator wants to display a 3D road map, he/she presses the road map button of the input device 28. The final X-ray image sensed by the X-ray imaging mechanism 10 is displayed on the X-ray image display 39. When the road map button is pressed, the corresponding 3D non-blood vessel CTA data stored in the 3D image memory 29 is read out. In this case, if there are 3D CTA images for a plurality of examinations (3D non-blood vessel image data and 3D blood vessel image data are handled as one examination data), the 3D blood vessel image data are displayed in a thumbnail form, and the operator selects target data from the thumbnail images. The selected 3D non-blood vessel image data is supplied to the projection processing unit 40. The projection processing unit 40 generates a non-blood vessel projection image by performing projection processing for the 3D non-blood vessel image data at the same projection angle (projection angle, SID) as that of the imaging posture of the X-ray imaging mechanism 10 (θA, θB, θC, SID). At this time, in generating CTA data, a projection image is generated assuming that the center of a CTA image is located at the intersection between the optical axis of the X-ray optical system (the axis connecting the focal point of the X-ray tube 12 to the center of the X-ray detector 14) and a plane located higher than the bed by D [cm]. In this case, first of all, the projection processing unit 40 generates a projection image upon adding a bias value to a CT value and transforming the value of an air portion into 0. In this case, D represents data obtained by reducing the actual size of the CTA image to ½. In addition, in generating a projection image, projection data is generated such that the upward direction of the projection image always coincides with the direction of the top of the patient head.

The positional shift identifying unit 34 identifies the positional shift amount of a non-blood vessel projection image with respect to the final X-ray image in the following two steps. In the first step, for example, an edge enhancement filter is applied to the data generated by the filtering unit 31 and the final X-ray image, and an approximate enlargement ratio and position are identified first by minimizing the following result:

$$CR(M, \Delta i, \Delta j) = \sum_{i=1}^{N} \sum_{j=1}^{N} [r\{X_E(i, j) + P(Mi + \Delta i, Mj + \Delta j)\}]^2 \quad (1)$$

where $X_E(i, j)$ and $P(Mi+\bullet i, Mj+\bullet j)$ are the edge-enhanced final X-ray image and the edge-enhanced non-blood vessel projection image, respectively, N is the matrix size of the image, M is the image enlargement ratio of the non-blood vessel projection image data, ($\bullet i$, $\bullet\bullet j$) is a shift vector, and CR(M, $\bullet i$, $\bullet\bullet j$) is the result of correlation computation. A correlation computation result is obtained while M is shifted from $M_1$ to $M_2$ and each of $\bullet i$ and $\bullet\bullet j$ is shifted from $-\bullet$ to $\bullet\bullet$, and an image enlargement ratio and shift vector which minimizes the correlation computation result are identified. In addition, r(x) is defined as follows:

$$r(x) = \begin{cases} x: X(i, j) \neq 0 \\ 0: X(i, j) = 0 \end{cases} \quad (2)$$

In this case, the following processing will be described on the assumption that $(M_0 \bullet i_0 \bullet\bullet j_0)$ is a condition under which CR(M, $\bullet i$, $\bullet\bullet j$) is minimized.

In the second step, a projection angle shift is identified in addition to the enlargement ratio and shift amount approximately identified in the first step. Although a projection angle can be mechanically obtained, it may often vary depending on the posture in imaging operation, a mechanical error, and the like. For this reason, a correlation computation result is obtained in the same manner as equation (1) while a mechanically measured projection angle (θRL, $θ_{OC}$) is shifted from $-\Delta θ$ to $\Delta θ$ and M, $\bullet i$, and $\bullet\bullet j$ are shifted, and a projection angle, image enlargement ratio, and shift vector which minimize the correlation computation result are identified. Note that since global searches for $\bullet$, $\bullet i$, and $\bullet\bullet j$ have been done to a certain extent in the first step, estimation is performed while the corresponding values are finely shifted in narrower ranges.

When the positional shift amount is identified, the projection processing unit 40 generates a blood vessel projection image (road map) from the 3D blood vessel image data by projection processing in accordance with the projection angle determined by the imaging posture and the calculated projection angle shift amount. The affine transformation unit 32 performs enlargement processing for this blood vessel projection image (road map) to allow matching with an enlargement ratio and shifts the image in accordance with the shift amount to allow spatial matching. The image combining unit 35 combines a road map having undergone positional shift correction with the final X-ray image. A hue is assigned to the combined image by the lookup table 37. The resultant image is displayed on the display 39.

When the acquisition of an X-ray image is resumed (fluoroscopy resumption), an X-ray image is replaced by a real-time image. At this time, a general X-ray image is displayed on one display, and a combined image is displayed on another display. The X-ray image combined with the image on another display is subjected to similar image processing (inverted first and then subjected to low-frequency reduction filtering).

If a patient moves during examination, X-ray image acquisition is stopped, and the calibration button is pressed. The final sensed X-ray image and the corresponding non-blood vessel image are sent to the positional shift identifying unit 34 and the like again, and the second step is resumed. After the execution of the second step, a positional shift amount is transmitted to the image combining unit 35, thereby allowing the generation of a road map in the same manner as described above.

Note that automatic and manual calibration modes are provided. When the manual mode is selected, the image obtained by inverting an X-ray image first and then applying edge enhancement filtering to it and the image obtained by applying edge enhancement filtering to the data obtained by projecting a non-blood vessel image on the basis of the positional shift amount at the current time point are combined/displayed in different colors. The operator can finely adjust a projection angle, image enlargement ratio, and shift vector while watching the combined display window.

(First Modification)

In the above embodiment, the image combining unit 35 combines the projection image represented by 3D blood vessel image data and an X-ray image into one window and displays it. However, the blood vessel projection image (road map) may be placed and displayed adjacent to the upper, lower, left, or right side of the X-ray image. At this time, in addition, the distal end portion of the guide wire or catheter may be detected from the X-ray image, and the detected position may be superimposed and displayed as a blinking light spot on the road map. In this case, superimposing the road map and the light spot in different colors can improve visibility. A distal end detection means for a guide wire or catheter may extract the data of the distal end portion of the guide wire by matched filtering or by using a marker for the catheter, or may extract the distal end portion by using a recently developed catheter having a GPS function.

(Second Modification)

In the above embodiment, the image combining unit 35 combines the projection image (road map) represented by 3D blood vessel image data and an X-ray image into one window and displays it. However, the present invention is not limited to this. 3D non-blood vessel image data, 3D blood vessel image data, and an X-ray image are transmitted to the imaging combining unit, and the following image is generated first by using the 3D non-blood vessel image data and the X-ray image:

$$S(i,j)=X(i,j)+\alpha \times B(i,j)-N \quad (3)$$

where $X(i, j)$ and $B(i, j)$ are an X-ray image and the projection image (road map) represented by 3D non-blood vessel image data, and $\alpha$ and $N$ are parameters representing transparency and brightness, respectively. At first, predetermined parameters are used. These parameters can be adjusted as needed. If the operator wants to see the information of a bone, $\alpha$ may be reduced. If the operator wants to display the bone with low density, $\alpha$ may be increased (note however that if $\alpha$ is increased too much, the information of the 3D non-blood vessel image data becomes dominant). Increasing $N$ makes the overall image dark, and vice versa. $S(i, j)$ basically represents an X-ray image. By adjusting $\alpha$ and $N$, the X-ray image can be displayed without change or at low density. Finally, this image is combined with a blood vessel projection image obtained by coloring $S(i,j)$ and displayed instead of the X-ray image subjected to image processing in the first embodiment.

(Third Modification)

In the above embodiment, the image combining unit 35 combines the projection image represented by 3D blood vessel image data and an X-ray image into one image and displays it. However, displaying an associated image between 3D blood vessel image data and an X-ray image by transmitting 3D non-blood vessel image data, the 3D blood vessel image data, and the X-ray image to the image combining unit and simultaneously combining and displaying the projection image represented by the 3D non-blood vessel image data and an inverted X-ray projection image in different colors allow the operator to refer to a 3D road map upon checking the positioning accuracy. In addition, the operator can determine, concerning the manual correction means in the first embodiment, on the basis of this combined image whether manual correction is required.

(Fourth Modification)

In the third modification, the projection image represented by 3D non-blood vessel image data and an inverted X-ray projection image are combined in different colors. However, edge enhancement processing may be applied to the projection image represented by 3D non-blood vessel image data and the inverted X-ray projection image, and the two edge-enhanced images may be combined and displayed in different colors. A positional relationship shift is dominantly recognized at an edge portion. That is, enhancing this information makes it possible to facilitate comprehension of a positional shift.

(Fifth Modification)

In the third modification, the projection image represented by 3D non-blood vessel image data and an inverted X-ray projection image are combined in different colors. However, the projection image represented by 3D non-blood vessel image data and the inverted X-ray projection image may be subtracted from each other, and the resultant image may be displayed. A positional relationship shift can also be effectively comprehended by the difference between them. Displaying this information makes it possible to facilitate comprehension of the positional shift.

(Sixth Modification)

Figure 4:
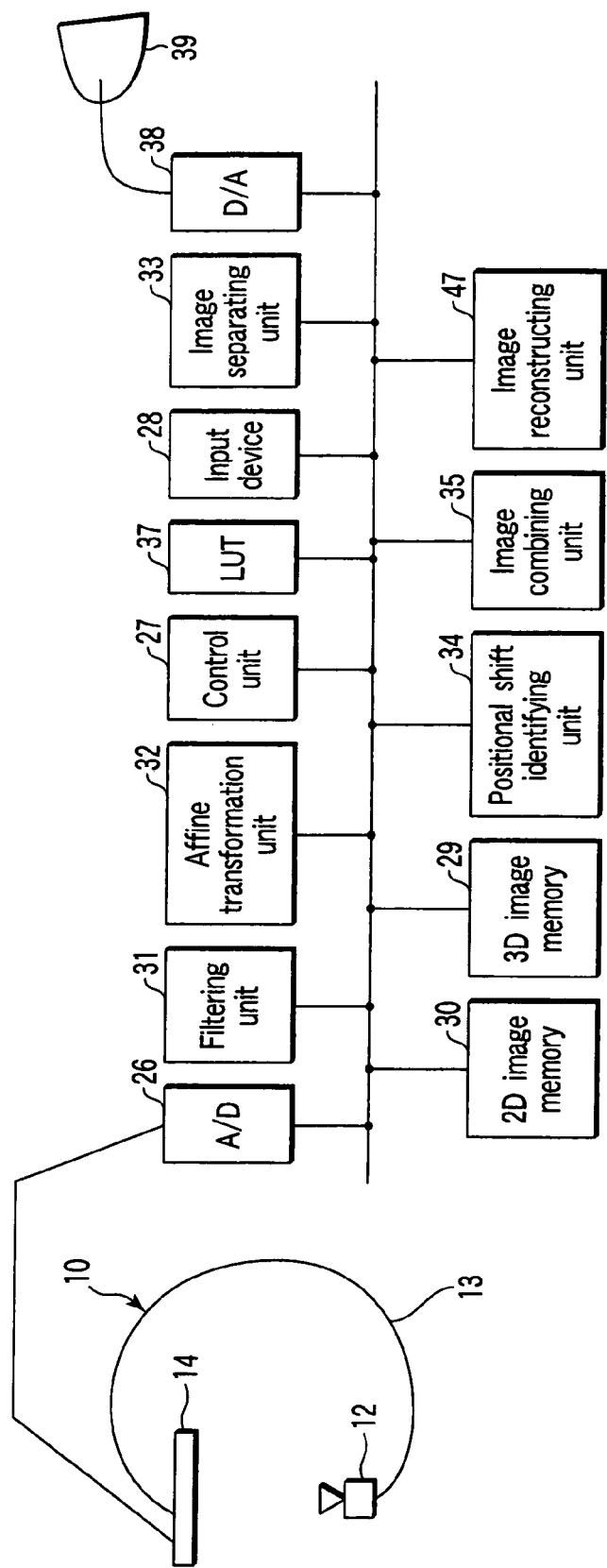
FIG. 4 is a view showing the arrangement of an X-ray diagnostic apparatus according to a modification of the present invention.

FIG. 4 shows the arrangement of a system according to the sixth modification. A description of the same part as that of the first embodiment will be omitted. An image reconstructing unit 47 reconstructs a 3D image on the basis of a plurality of X-ray images which are repeatedly acquired by the X-ray imaging mechanism 10 in different imaging postures. There are three 3D reconstruction modes: a 3D-DA mode of performing reconstruction processing on the basis of rotational DA images (rotational digital angio images); a pseudo 3D-DA mode of performing reconstruction processing by using a contrast sequence of rotational DSA images (rotational digital subtraction angio images); and a mode of separately reconstructing a 3D blood vessel image from rotational DSA images and a 3D non-blood vessel image from a rotational DSA mask sequence.

The image reconstructing unit 47 performs 3D reconstruction. In the first step, subtraction is performed. When a rotational DSA image is to be reconstructed, a contrast image at the corresponding angle is subtracted from a mask image. For images corresponding to other imaging angles, calibration data are subtracted from the respective data. In this case, calibration data is data for correcting the sensitivity of the detector and an X-ray distribution, and is obtained in advance. As an example of a reconstruction method, the filtered back projection method proposed by Feldkamp et al. will be described below. A proper convolution filter like the one used by Shepp & Logan or Ramachandran is applied to subtraction images of 200 frames. Back projection computation is then performed for the images to obtain reconstructed data. In this case, a reconstruction region is defined as a cylinder inscribed in an X-ray beam in all directions of the X-ray tube. The interior of this cylinder must undergo 3D discretization according to a length d of the central portion of the reconstruction region projected on the width of one detection element of the detector, and a reconstructed image must be obtained from data at discrete points. This discretization interval is an example and may change depending on the apparatus and maker. Basically, therefore, the discretization interval defined by each apparatus may be used.

A reconstructed image is processed for each mode as follows.

1) 3D-DA Mode/Pseudo 3D-DA Mode

Like a CTA image, a reconstructed 3D-DA image or pseudo 3D-DA image is separated into a 3D non-blood vessel image and a 3D blood vessel image by the image separating unit 33 in the same manner as described above. These images are then sent to the 3D image memory 29. Note that a blood vessel extraction threshold for the 3D-DA mode is set at this time, and a 3D blood vessel image is extracted by using the threshold.

2) Separate Reconstruction Mode

A 3D non-blood vessel image and a 3D blood vessel image are sent as a pair to the 3D image memory 29. Positional shift identification and image combining are performed in the same manner as in CTA.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
   an X-ray imaging unit including an X-ray tube and an X-ray detecting unit configured to generate an X-ray image;
   an image generating unit configured to generate a 3D non-blood vessel image and a 3D blood vessel image from an original 3D image generated by the X-ray diagnostic apparatus or an X-ray CT apparatus;
   a projection image generating unit configured to generate a non-blood vessel projection image from the 3D non-blood vessel image and to generate a blood vessel projection image from the 3D blood vessel image;
   a positional shift identifying unit configured to identify a positional shift between the X-ray image and the non-blood vessel projection image;
   a correcting unit configured to correct the blood vessel projection image on the basis of the positional shift; and
   a display unit configured to display the X-ray image and the corrected blood vessel projection image.

2. An apparatus according to claim 1, wherein the X-ray image is a real-time image.

3. An apparatus according to claim 1, wherein the original 3D image is a CT contrast image.

4. An apparatus according to claim 1, wherein the original 3D image is a rotational X-ray contrast image.

5. An apparatus according to claim 1, wherein the image generating unit generates the non-blood vessel image from the original 3D image by threshold processing based on CT values.

6. An apparatus according to claim 1, further comprising a reconstructing unit which reconstructs the 3D non-blood vessel image from a plurality of X-ray images generated by the X-ray imaging mechanism at different imaging angles.

7. An apparatus according to claim 1, further comprising a reconstructing unit which reconstructs the 3D non-blood vessel image from a plurality of mask images generated by the X-ray imaging mechanism at different imaging angles under a rotational contrast imaging sequence.

8. An apparatus according to claim 1, wherein the image generating unit generates the 3D blood vessel image from the original 3D image by threshold processing.

9. An apparatus according to claim 1, further comprising a reconstructing unit which reconstructs a 3D DA image from a rotational X-ray contrast image generated by the X-ray imaging mechanism, and an extracting unit which extracts a 3D blood vessel image from the 3D DA image on the basis of voxel values.

10. An apparatus according to claim 1, further comprising a reconstructing unit which reconstructs the 3D blood vessel image from a DSA image of a rotational X-ray contrast image generated by the X-ray imaging mechanism.

11. An apparatus according to claim 1, further comprising a reconstructing unit which reconstructs the 3D blood vessel image from a rotational X-ray contrast image generated by the X-ray imaging mechanism under a contrast sequence, and a reconstructing unit which reconstructs the 3D non-blood vessel image from a rotational X-ray contrast image generated by the X-ray imaging mechanism under a masked sequence.

12. An apparatus according to claim 1, wherein the positional shift identifying unit identifies an angle difference between the X-ray image and the non-blood vessel projection image, an image enlargement ratio difference between the X-ray image and the non-blood vessel projection image, and a position difference between the X-ray image and the non-blood vessel projection image.

13. An apparatus according to claim 12, further comprising an input device for manual fine adjustment of a positional shift between the X-ray image and the non-blood vessel projection image.

14. An apparatus according to claim 1, wherein the display unit arranges and displays the X-ray image and the corrected blood vessel projection image at the same observation angle and the same position on a window.

15. An apparatus according to claim 14, wherein the display unit superimposes and displays a characteristic feature of the X-ray image on the corrected blood vessel projection image.

16. An apparatus according to claim 15, wherein the characteristic feature is a marker attached to a distal end of the device or to the device.

17. An apparatus according to claim 1, wherein the display unit superimposes and displays the corrected blood vessel projection image on the X-ray image.

18. An apparatus according to claim 1, further comprising a subtraction processing unit which subtracts the 3D non-blood vessel image from the X-ray image.

19. An apparatus according to claim 18, wherein the display unit superimposes and displays a subtraction image obtained by the subtraction processing unit on the 3D blood vessel image.

20. An apparatus according to claim 18, wherein the subtraction processing unit has a function of subtracting a projection image of the 3D non-blood vessel image from the X-ray image in accordance with an arbitrary weighting coefficient.

21. An apparatus according to claim 1, wherein the display unit combines and displays the non-blood vessel projection image on the X-ray image.

22. An apparatus according to claim 21, wherein the display unit superimposes and displays the non-blood vessel projection image on the X-ray image in different colors.

23. An apparatus according to claim 21, wherein the display unit edge-enhances, combines, and displays the 3D non-blood vessel image and the X-ray image.

24. An apparatus according to claim 1, wherein the display unit displays a subtraction image based on a projection image of the 3D non-blood vessel image and the X-ray image.

25. An X-ray diagnostic apparatus, comprising:

an X-ray imaging unit including an X-ray tube and an X-ray detecting unit configured to generate an X-ray image;

an image generating unit configured to generate a 3D non-blood vessel image and a 3D blood vessel image from an original 3D image generated by the X-ray diagnostic apparatus or an X-ray CT apparatus;

a projection image generating unit configured to generate a non-blood vessel projection image from the 3D non-blood vessel image and to generates a blood vessel projection image from the 3D blood vessel image;

a positional shift identifying unit configured to identify a positional shift between the X-ray image and the non-blood vessel projection image;

a correcting unit configured to correct a positional shift of the blood vessel projection image on the basis of the positional shift; and a combining unit configured to combine the X-ray image and the corrected blood vessel projection image.

26. An X-ray diagnostic apparatus, comprising:

an X-ray imaging unit including an X-ray tube and an X-ray detecting unit configured to generate an X-ray image;

an image generating unit configured to generate a 3D non-blood vessel image and a 3D blood vessel image from an original 3D image generated by the X-ray diagnostic apparatus or an X-ray CT apparatus;

a projection image generating unit configured to generate a non-blood vessel projection image from the 3D non-blood vessel image and to generates a blood vessel projection image from the 3D blood vessel image;

a positional shift identifying unit configured to identify a positional shift between the X-ray image and the non-blood vessel projection image; and a combining unit configured to combine the X-ray image and the blood vessel projection image on the basis of the positional shift.

27. An image processing apparatus, comprising:

a storage unit configured to store an X-ray image, 3D non-blood vessel image, and 3D blood vessel image associated with the same subject;

a projection image generating unit configured to generate a non-blood vessel projection image from the 3D non-blood vessel image and to generates a blood vessel projection image from the 3D blood vessel image;

a positional shift identifying unit configured to identify a positional shift between the X-ray image and the non-blood vessel projection image; and a combining unit configured to combine the X-ray image and the blood vessel projection image on the basis of the positional shift.

* * * * *